United States Patent [19]

Paspek, Jr.

[11] Patent Number: 4,465,888
[45] Date of Patent: Aug. 14, 1984

[54] OLIGOMERIZATION OF OLEFINS IN SUPERCRITICAL WATER

[75] Inventor: Stephen C. Paspek, Jr., North Royalton, Ohio

[73] Assignee: The Standard Oil Company, Cleveland, Ohio

[21] Appl. No.: 485,094

[22] Filed: Apr. 14, 1983

[51] Int. Cl.³ .............................................. C07C 3/02
[52] U.S. Cl. .................... 585/520; 585/510; 585/732; 526/80; 526/84
[58] Field of Search .................. 585/510, 520, 732; 526/80, 84

[56] References Cited

U.S. PATENT DOCUMENTS 2,214,463  9/1940  Ipatieff et al. .
2,422,692  6/1947  Mattox .
3,948,754  4/1976  McCollum et al. .
4,082,910  4/1978  Buechner et al. .................. 585/510
4,087,602  5/1978  Mietzner et al. .................. 585/510

FOREIGN PATENT DOCUMENTS 129807  12/1945  Australia ............................. 585/520
612056   4/1947  United Kingdom ............... 585/520

*Primary Examiner*—Delbert E. Gantz
*Assistant Examiner*—A. Pal
*Attorney, Agent, or Firm*—Salvatore P. Pace; David J. Untener; Larry W. Evans

[57] ABSTRACT

Fuel range liquid hydrocarbons are produced by the oligomerization of olefins in a process comprising contacting the olefins containing 5 or less carbon atoms with a water containing medium at a temperature sufficient to cause oligomerization and at a pressure sufficient to maintain the density of the medium at about 0.5 to about 1.0 grams per milliliter.

15 Claims, No Drawings

OLIGOMERIZATION OF OLEFINS IN SUPERCRITICAL WATER

BACKGROUND OF THE INVENTION

1. Field of the Invention

This invention relates to the oligomerization of olefins into light, liquid transportation fuels. More specifically, this invention relates to the oligomerization of olefins in a water containing medium.

2. Description of the Prior Art

In the 1930's, gasoline range liquids were produced by reacting olefins. This "polymer gasoline" was made by heating olefins at high temperatures under high pressure. However, due to the exothermic nature of the process these processes were extremely difficult to control. It was not uncommon to have the reaction temperature jump from 800° F. to over 1200° F. in a manner of minutes. The high temperatures and pressures of these processes also left the reaction vessel coated with a powdery coke.

Improvements made to the above process have largely entailed the addition of catalysts. An example of one such process is described in U.S. Pat. No. 2,422,692 which discloses a process for producing isobutane and other liquid hydrocarbons from propylene and other gaseous olefins. This reaction is carried out over a polarizing catalyst at a temperature of from 200° C. to 500° C. and at a pressure of from 100 psi to 1000 psi.

The instant invention pertains to dense, water containing fluids at elevated temperatures and pressures. In part, the instant invention pertains to the use of supercritical fluids. A fluid which is at both a temperature and pressure exceeding its critical temperature and pressure is a supercritical fluid. A supercritical fluid exists as a form of matter in which its liquid and gaseous states are indistinguishable from one another. The critical temperature of a fluid is the temperature above which that fluid cannot be liquified by an increase in pressure. The critical pressure of a fluid is simply the pressure of the fluid at its critical temperature. Water, for example, is a supercritical fluid when its temperature and pressure exceed 274.2 C. and 3204 psi (218.3 atm).

In recent years supercritical fluids have found use in a wide variety of applications. Supercritical fluids have been used for upgrading heavy crude oil and residual oils, for removing the mineral matter from liquified coal, and for dissolving and oxidizing hazardous organic chemical wastes. In use with olefins, supercritical water has exhibited potential to transform large olefins into other products. In U.S. Pat. No. 3,948,754, which relates to a process employing supercritical water and a catalyst for the recovery and upgrading of hydrocarbons from oil shale and tar sands, it was disclosed that supercritical water acting with an $RuCl_3$ catalyst successfully yielded substantial quantities of octane from octene without the production of higher molecular weight species.

SUMMARY OF THE INVENTION

It has been discovered that a water containing medium facilitates the oligomerization of normally gaseous olefins into fuel range paraffinic liquid hydrocarbons. These liquid hydrocarbons are produced from olefins in a process comprising contacting olefins containing five or less carbon atoms with a water containing medium at a temperature sufficient to cause oligomerization and at a pressure sufficient to maintain the density of the medium at about 0.5 to about 1.0 grams per milliliter.

DESCRIPTION OF THE INVENTION

An oligomer is a polymer molecule consisting of several monomeric units. This invention relates to oligomers formed from olefins containing 5 or less carbon atoms. Representative of the olefins of use in this invention are ethylene, propylene, butylene, butadiene and various pentenes as well as isomers and substituted derivatives of these compounds. Typically these olefins are gaseous by-products resulting from cracking operations. However, olefins containing 5 or less carbon atoms and derived from any source may be utilized in this invention.

The olefins employed in the instant invention do not require a high degree of purity. The olefins may constitute a fraction of a feedstock containing a wide range of organic and inorganic matter. It is possible to use ordinary refinery streams, such as coker-off-gas or retort off-gas, without special preparation. The instant invention may even be employed for feedstreams containing olefins in quantities so small as to not be economically feasible to recover by known methods.

Olefins are oligomerized while in contact with a water containing medium. The oligomerization occurs in a mixture which is substantially a one phase medium. This medium is not liquid or gaseous in the common meaning of these terms, but is best described in terms of its density. The medium has a density of about 0.05 to about 1.0 grams per milliliter. More preferably, the medium has a density of about 0.1 to about 0.4 grams per milliliter. Most preferably the medium has a density of about 0.2 to about 0.3 grams per milliliter.

In order to obtain the density required for the water containing medium, the medium must be at elevated temperatures and pressures. At room temperatures and atmospheric pressure, olefins and water are not fully miscible. However, olefins are easily miscible in a water containing medium at elevated temperatures and pressures especially those near the critical temperature and pressure of water. Therefore, temperatures and pressures approaching or greater than the critical temperature and pressure for water are most suitable for this process.

While not wishing to be bound by theory, it is believed that the water containing medium functions as a catalyst, a reactant and as a means to control the rate of reaction and rate of heat transfer from the system. As a catalyst, the water containing medium moderates both free radical and ionic mechanisms. As a reactant, supercritical water is a donor of hydrogen for saturating double bonds. This is evidenced by the resulting liquid hydrocarbons being largely paraffinic and the existence of carbon monoxide and carbon dioxide in the gaseous effluent from the reactor. Since water is a donor of hydrogen, no externally supplied hydrogen is required for the instant process.

The oligomerization of olefins is a highly exothermic reaction. The water containing medium can be used to control the rate of oligomerization by adjustments in the water to olefin ratio. The water containing medium also increases the rate of heat transfer from the system.

It is also theorized that in the instant process, there are two competing reactions, the oligomerization of olefins into liquids and the thermal degradation of paraffinic liquids into saturated gases. The water containing medium appears to suppress the thermal degradation reaction and there appears to be an upper limit on the extent of oligomerization in the instant process. The normally liquid hydrocarbons produced by the instant process contain 4 to 20 carbon atoms and nearly all are saturated hydrocarbons. These products are also highly branched.

Yields of liquid hydrocarbons, as a weight percent of olefins originally introduced into the reactor, as high as 72 percent have been achieved. However the yield is dependent upon several interrelated operational parameters. These parameters are temperature, pressure, residence time, the nature and concentrations of the olefins and the desired product.

Temperatures sufficient to cause oligomerization of the olefins are suitable for the instant invention. Suitable temperatures are greater than 200° C. Pressures sufficient to maintain a density for the water containing medium of at least 0.05 grams per milliliter are suitable for this process. Suitable pressures are greater than 0 psig. Generally as the process temperature increases, the pressure must also be increased to maintain the desired density of the water containing medium. Generally the yield of liquid hydrocarbons will increase as the temperature and pressure approaches and exceeds the critical temperature and pressure of water. Preferred temperature and pressures are those sufficient for oligomerization in a water containing medium with a density of about 0.05 grams per milliliter to about 1.0 grams per milliliter. More preferred temperatures and pressures are those sufficient for oligomerization in a water containing medium with a density of about 0.1 grams per milliliter to about 0.4 grams per milliliter. Most preferred temperatures and pressures are those sufficient for oligomerization in a water containing medium of about 0.2 to 0.3 grams per milliliter. While a broad range of temperatures and pressures is sufficient to cause oligomerization and yield the desired medium density, an example of typical operating conditions for the instant process are temperatures between 375° C. and 500° C. and pressures of at least 2000 psi.

The residence time is the amount of time the olefins are in contact with the water containing medium at process conditions in order to produce liquid hydrocarbons. Optimum residence time is dependent upon the other operational parameters. Generally, for a specific temperature and pressure the degree of oligomerization increases with residence time. Preferred residence times range from about one minute to six hours. More preferred residence times range from about three minutes to about three hours. Most preferred residence times range from about five minutes to about one hour.

Typically, the water to olefin weight ratios are about 0.25:1 to about 50:1. Preferably the ratio is about 0.7:1 to about 7:1 and more preferably about 1:1 to about 2:1.

The process of the instant invention may be done in batch or in a continuous flow reactor. In either case the reactor should be able to withstand several thousands pounds of pressure and be equipped with a means for mixing of the olefin and the water containing medium. In this process, the reactor is first purged with an inert gas, e.g. argon, nitrogen or steam, in order to yield the reactor substantially free of oxygen. Next, the olefins and water are fed into the reactor. These may be introduced in separate or combined feeds, and either or both may be subjected to preheating. The reactants are then mixed and heated to a temperature sufficient to cause oligomerization.

The product of both bulk and continuous flow reactors includes liquid hydrocarbons, carbon monoxide, carbon dioxide, unreacted olefins and gaseous alkanes. These products are separated by conventional techniques. Typically, any unreacted olefins are recycled.

An advantage to the oligomerization of olefins in a water containing medium is that little or no coke is produced inside the reactor. This is a major benefit. Coke tends to foul conventional reactors and where coke is produced the reactors must be shut down regularly and cleaned. The absence of coke in this invention means that these reactors are capable of being operated continuously. Lastly, no coke allows for the easier separation of the reactor products.

SPECIFIC EMBODIMENTS

The following Examples are provided in order to better illustrate the instant invention. In each of the Examples the reactor product was analyzed using a gas chromatograph in order to determine product composition and relative quantities of each component.

EXAMPLE I

A 4:1 weight ratio of water and ethylene were metered into a 300 cc stainless steel stirred autoclave. The unit was heated at 427° C. for 1 hour, at an average internal pressure of 4900 psig. A 72 weight percent yield of light liquids was realized, with no coke or residual oil formation.

EXAMPLE II

A 1.5:1 weight ratio of water and isobutylene were metered into a 300 cc stainless steel stirred autoclave. The unit was heated at 400° C. for 1 hour at an average internal pressure of 5500 psig. A 64 weight percent yield of light liquids was realized, with no coke or residual oil formation.

EXAMPLE III

A mixture of ethylene and pentane and water were loaded into the 300 cc stainless steel stirred autoclave to give a water-to-hydrocarbon weight ratio of about 1. The unit was heated to 360° C. for 60 minutes at an average internal pressure of 4935 psig. Approximately 28 weight percent of the olefin polymerized to form light oils, with no coke or residual oil formation.

EXAMPLE IV

A mixture of ethylene and methane and water were loaded into the 300 cc stainless steel stirred autoclave to give a water-to-hydrocarbon weight ratio of about 7. The unit was heated to 425° C. for 60 minutes at an average internal pressure of 5311 psig. Approximately 44 weight percent of the olefin polymerized to light oil, with no residual oil formation, and only a trace of coke.

EXAMPLE V

Coker off-gas containing about 25–30 weight percent light olefins was loaded into the 300 cc stainless steel stirred autoclave with water to give a water-to-hydrocarbon ratio of about 6:1. The unit was heated to 425° C. for 60 minutes at an average pressure of 5328 psig. Much of the olefin polymerized to light oils.

Although only a few embodiments of this invention have been described above, it should be appreciated that many additions and modifications can be made without departing from the spirit and scope of the invention. These and all other modifications are intended to be included within the scope of this invention, which is to be limited only by the following claims.

The claimed invention is:

1. A process for the oligomerization of olefins containing five or less carbon atoms to produce liquid hydrocarbons containing four to twenty carbon atoms, the process comprising contacting the olefins with a water containing medium at a temperature of greater than 200° C. and a pressure from 0 to 7,000 psi whereby the temperature and pressure are sufficient to maintain the mixture of olefins and water containing medium about at or above the critical temperature and pressure of the mixture.

2. The process of claim 1, where the density of the water containing medium is about 0.05 to about 1.0 grams per milimeter.

3. The process of claim 1, where the density of the water containing medium is about 0.1 to about 0.4 grams per milliliter.

4. The process of claim 3, where the density of the water containing medium is about 0.2 to about 0.3 grams per milliliter.

5. The process of claim 1, where the olefins are in contact with the water containing medium at oligomerization conditions for a period of time in the range of about one minute to about six hours.

6. The process of claim 5, where the olefins are in contact with the water containing medium at oligomerization conditions for a period of time in the range of about three minutes to about six hours.

7. The process of claim 6, where the olefins are in contact with the water containing medium at oligomerization conditions for a period of time in the range of about five minutes to about one hour.

8. The process of claim 1, where the water to olefin weight ratio is about 0.25:1 to about 50:1.

9. The process of claim 8, where the water to olefin weight ratio is about 0.7:1 to about 7:1.

10. The process of claim 9, where the water to olefin weight ratio is about 1:1 to about 2:1.

11. The process of claim 1, where the temperature is about 375° C. to about 500° C. and the pressure is at least about 2000 psi.

12. The process of claim 1, where the olefins reacted in the process are introduced into the process in a feedstream with an olefin content of less than 100 percent.

13. The process of claim 12, where the olefins reacted in the process are introduced into the process in a refinery stream of coker off-gas or retort off-gas.

14. The process of claim 1 where the oligomerization occurs in a batch reactor.

15. The process of claim 1 where oligomerization occurs in a continuous flow reactor.

* * * * *